United States Patent
Antebi et al.

(10) Patent No.: US 9,149,041 B2
(45) Date of Patent: Oct. 6, 2015

(54) STABILIZED AND ACTIVATED BROMINE SOLUTIONS AS A BIOCIDE AND AS AN ANTIFOULING AGENT

(75) Inventors: Shlomo Antebi, Haifa (IL); Chen Zolkov, Kiryat Tivon (IL); David Feldman, Haifa (IL)

(73) Assignee: Bromine Compounds Ltd., Beer-Sheva (IL)

( * ) Notice: Subject to any disclaimer, the term of this patent is extended or adjusted under 35 U.S.C. 154(b) by 0 days.

(21) Appl. No.: 13/322,469

(22) PCT Filed: Jun. 7, 2010

(86) PCT No.: PCT/IL2010/000447
§ 371 (c)(1),
(2), (4) Date: Nov. 25, 2011

(87) PCT Pub. No.: WO2010/143183
PCT Pub. Date: Dec. 16, 2010

(65) Prior Publication Data
US 2012/0121728 A1    May 17, 2012

Related U.S. Application Data

(60) Provisional application No. 61/184,863, filed on Jun. 8, 2009.

(51) Int. Cl.
  *A01N 59/00* (2006.01)
  *A01P 1/00* (2006.01)
  *A01N 47/28* (2006.01)

(52) U.S. Cl.
  CPC ..................................... *A01N 47/28* (2013.01)

(58) Field of Classification Search
  CPC ....... A01N 59/00; A01N 25/22; A01N 59/08; C02F 1/766; C02F 2209/06; C11D 3/395
  See application file for complete search history.

(56) References Cited

U.S. PATENT DOCUMENTS

| 4,212,853 | A | | 7/1980 | Fukui | |
|---|---|---|---|---|---|
| 5,415,803 | A | | 5/1995 | Shorr | |
| 5,558,503 | A | * | 9/1996 | Weller et al. | 417/307 |
| 6,270,722 | B1 | * | 8/2001 | Yang et al. | 422/37 |
| 6,375,991 | B1 | * | 4/2002 | Moore, Jr. | 424/703 |
| 6,506,418 | B1 | * | 1/2003 | McKinnie et al. | 424/703 |
| 2002/0014463 | A1 | | 2/2002 | Iverson et al. | |
| 2002/0056689 | A1 | * | 5/2002 | Shim et al. | 210/756 |
| 2005/0061197 | A1 | * | 3/2005 | Nalepa | 106/15.05 |
| 2005/0147528 | A1 | | 7/2005 | Shim et al. | |
| 2006/0003028 | A1 | * | 1/2006 | Myers et al. | 424/723 |
| 2007/0098817 | A1 | | 5/2007 | Wetegrove et al. | |
| 2008/0041789 | A1 | | 2/2008 | Bornak et al. | |
| 2008/0047904 | A1 | * | 2/2008 | Carpenter | 210/747 |

FOREIGN PATENT DOCUMENTS

EP    0570044    11/1993

OTHER PUBLICATIONS

FTA, "Ozone Treatment for Cooling Towers", produced for U.S. Department of Energy by the Pacific Northwest National Laboratory, 1995.*
Grobe, K.J, Zahller, J and Stewart P.S., 2002 in "Role of dose concentration in biocide efficacy against Pseudomonas aeruginosa Biofilms", J. Industrial Microbiology & Biotechnology, vol. 29, pp. 10-15.
Organic Syntheses. Coll. vol. 5, p. 184 (1973); vol. 49, p. 9 (1969).].
[S. S. Israelstam, J. S. African Chem. Inst. (1956), 9, 30-32.
J.S. Chaltsy S. S, Israelstam, Chem. Ind (1954), 1452-53.

* cited by examiner

*Primary Examiner* — Robert T Crow
*Assistant Examiner* — John P Nguyen
(74) *Attorney, Agent, or Firm* — Roach Brown McCarthy & Gruber, P.C.; Kevin D. McCarthy

(57) ABSTRACT

The invention provides a process of removing or preventing biofouling, particularly on surfaces of industrial and agricultural equipment in contact with aqueous liquids. The process employs an antifouling composition of stabilized active halogen having a low pH.

12 Claims, No Drawings

STABILIZED AND ACTIVATED BROMINE SOLUTIONS AS A BIOCIDE AND AS AN ANTIFOULING AGENT

REFERENCE TO CO-PENDING APPLICATIONS

This application claims priority as a 371 of international application PCT/IL2010/000447, filed on Jun. 7, 2010; which claims priority to U.S. provisional patent application Ser. No. 61/184,863, filed on Jun. 8, 2009.

FIELD OF THE INVENTION

The present invention relates to a method of reducing or preventing bio-contaminations and biofilm formation on surfaces in contact with aqueous liquids, utilizing stable concentrated aqueous solutions comprising a mixture of active halogen and urea derivatives.

BACKGROUND OF THE INVENTION

Elemental chlorine and bromine are effective biocides. However, their low solubility (less than 1 and 4 wt %, respectively), and increasing safety requirements as well, limit their use as a biocide in industrial applications. Aqueous solutions of active chlorine are widely used in bleaching processes, treatment of swimming pool water and as disinfectant. It is well known that upon addition to water, active oxidizer species of halogen comprise HOX, and XO$^-$ (where X stands for Cl or Br). The aqueous halogen solutions are susceptible to decomposition during storage and prior to use, losing their beneficial properties. An aqueous halogen solution is unstable and emits very pungent fumes. Mixtures of aqueous halogen solutions with stabilizers have been used, usually strongly alkaline, the stabilizers usually comprising sulfamate. EP 0570044 describes a stable solution of elemental bromine and urea in water for disinfection, bleaching, and etching.

Biofouling is an undesired accumulation of organisms or their products, or products of their decomposition in liquid volumes or on wet surfaces; particularly, biofouling comprises microorganisms, such as bacteria, fungi, algae, etc. Biofouling is found in almost all circumstances where water based liquids are in contact with other materials. Biofouling is controlled by a variety of methods, including coating the endangered surfaces, or applying biocides in their vicinity. It is an object of this invention to provide a simple, cheap, antifouling method.

It is another object of this invention to provide an antifouling method without using caustic alkali materials.

It is another object of this invention to provide an antifouling method utilizing concentrated compositions which can be easily and safely manipulated and diluted for use, and which are stable on prolonged storage.

It is still another object of this invention to provide an antifouling method utilizing active halogen compositions which are stable on prolonged storage and efficient when used as biocide.

It is a still other object of the invention to provide an efficient biocide for the treatment of water with high TOC content.

It is a further object of the invention to provide an efficient biocide for reducing or preventing bio-contaminations in aqueous liquids or on surfaces in contact with aqueous liquids, utilizing stable aqueous solutions comprising a mixture of active halogen and urea or its derivatives.

Other objects and advantages of present invention will appear as description proceeds.

SUMMARY OF THE INVENTION

The invention provides a process of removing or preventing biofouling in a volume of an aqueous liquid or on a surface in contact with an aqueous liquid, comprising i) providing an aqueous composition (antifouling composition) containing a halogen source and a urea derivative, wherein the molar ratio urea derivative/halogen is preferably at least 1/1, and the pH of said aqueous composition is acidic; ii) optionally diluting said composition obtained in step i) (stock solution) with water, thereby obtaining a working solution; and iii) contacting said volume or said surface with said stock solution or with said working solution. The term "urea derivative" as used herein is intended to include urea derivatives and urea as well. Said halogen source comprises an active bromine source or an active chlorine source selected from the group consisting of $Br_2$, BrCl, $Cl_2$, halogenated alkylhydantoins selected from BC-DMH, DC-DMH, DB-DMH, BC-MEH, DC-MEH, DB-MEH, and the likes, TCCA, Na-DCC, and a mixture of a bromide or HBr with an oxidizer. In the most preferred embodiment of the invention, provided is a process of removing or preventing biofouling in a volume of an aqueous liquid or on a surface in contact with an aqueous liquid, comprising providing an aqueous composition containing a urea derivative and an active bromine source, wherein the molar ratio or urea derivative to total bromine is preferably at least 2/1, and the pH value of said aqueous composition is preferably less than 4. In the first aspect of the invention, said process comprises the steps of i) mixing water, a urea derivative, and an active bromine source selected from the group consisting of $Br_2$, BrCl, BC-DMH, DB-DMH, and a mixture of a bromide or HBr with an oxidizer, wherein the molar ratio urea derivative/total bromine is at least about 2/1, thereby obtaining an aqueous composition of stabilized active bromine; ii) optionally diluting said composition obtained in step i) (stock solution) with water, thereby obtaining a working solution; and iii) contacting said volume or said surface with said stock solution or with said working solution. In the second aspect of the invention, said process comprises the steps of i) mixing water, a urea derivative, and an active chlorine source selected from the group consisting of $Cl_2$, TCCA, Na-DCC, and halogenated alkylhydantoins selected from BC-DMH, DC-DMH, BC-MEH, DC-MEH, and the likes, wherein the molar ratio urea/chlorine is preferably at least about 2/1, thereby obtaining an aqueous composition of stabilized active chlorine; ii) admixing to said stabilized active chlorine a bromide source, thereby obtaining an aqueous composition of stabilized active bromine; iii) optionally diluting said composition obtained in step ii) (stock solution) with water, thereby obtaining a working solution; and contacting said volume or said surface with said stock solution or with said working solution. Said step ii) may be performed after a prolonged period of storage of said aqueous composition of stabilized active chlorine, and at an appropriate time before said step iv). In a process according to the invention, the urea or urea derivative may be added in more portions; the urea or urea derivative may be added both to said stock solution and to said working solution.

The term "appropriate time" means a time period during which the concentration of active chlorine in said aqueous composition of stabilized active chlorine does not decrease below a desired minimal value, while said admixing the bromide source precedes the intended biocidal use closely enough, so that the active bromine concentration does not decrease below a desired minimal value. Said minimal desired values will take into consideration practical effective concentrations of active halogen for the intended uses, as well as the cost effectiveness of the process. Usually, it is desirable that the concentration of active chlorine in said aqueous composition of stabilized active chlorine does not decrease below 50% of the initial value, and that the concentration of active bromine in said aqueous composition of stabilized active bromine does not decrease below 50% of the initial value. The stability of said aqueous composition of stabilized active chlorine prepared in accordance with the invention is surprisingly high, and may comprise a half life (the time during which the active chlorine decreases to a half of its initial value) up to 5 years; said half life increases with the ratio of urea/active chlorine, as this ratio increases from ¼ to 40. The stability of the active bromine (as bromourea) in the compositions according to the invention is lower than the stability of active chlorine (in chlorourea), and therefore, in a process according to the invention, the conversion of active chlorine to active bromine (bromourea) is performed conveniently, at an appropriate time, before the use of the antifouling composition. Occasionally, converting said active chlorine to said active bromine in a process according to the invention is called "activating bromine". The stability of active bromine, or "activated bromine", in the compositions according to the invention may comprise a half life of up to months or even up to a year, increasing with the urea concentration, and further increasing as the ratio Br/Cl decreases. A skilled artisan will easily measure the stabilities of active chlorine and active bromine, and will also easily extrapolate the found values to desired time periods, according to practical needs, ensuring the most efficient and economic halogen concentrations. In the present context, the terms "active halogen", "active chlorine", and "active bromine" mean, respectively, halogen, chlorine, and bromine in the oxidation state other than minus one; the terms include, for example, elemental chlorine or bromine, as well as hypochlorite and hypobromite ions, but not chloride or bromide.

Said period of storage of said aqueous composition of stabilized active chlorine, before the conversion of active chlorine to active bromine, may be up to two years, but even longer. Said appropriate time, between the biocidal use and said activating, may be up to one year; the time may be much shorter, for example hours before the use. In a preferred embodiment of a process according to the invention, the molar ratio urea derivative/halogen is up to 40/1. In some embodiments of the invention, the ratio may be selected from the group consisting of 30/1, 20/1, 10/1, 5/1, 3/1, 2/1, and 1/1. Said bromide source is preferably selected from the group consisting of NaBr, KBr, HBr, and $NH_4Br$. Said stock solution comprises halogen in a concentration of 0.1-20 wt % (when expressed as total halogen), while said stock solution is stable on prolonged storage of up to one year. In a preferred embodiment, said aqueous composition of stabilized active chlorine has a concentration of up to 10 wt % (expressed as total $Cl_2$ in the composition), wherein said bromide source is added in an amount corresponding to a molar ratio of Br/Cl of from 0.1 to 2.0, preferably from about 0.5 to about 2.0. In one preferred embodiment, said aqueous composition of stabilized active chlorine has a concentration of up to 5 wt % (expressed as total $Cl_2$ in the composition), wherein said bromide source is added in an amount corresponding to a molar ratio of Br/Cl of from 1.0 to 2.0. In one embodiment, said bromide source is added in an amount corresponding to the molar ratio of from 0.1 to 1.0; the antifouling composition contains enough active bromine and may be stored before the use for relatively prolonged times (for example, up to months). In another embodiment, said bromide source is added in an amount corresponding to the molar ratio of about 2; the antifouling composition comprises a high concentration of active bromine, and should be preferably used within a shorter period (for example, within several weeks). Said working solution exhibits biocidal activity when diluted down to an active bromine concentration of 0.1 ppm. Said working solution exhibits biocidal activity when the active bromine decreases from higher values to a concentration of 0.1 ppm or more, during storage. Said stock solution has preferably a pH of less than 4. The pH is often lower than 2.

In one aspect of the invention, said aqueous composition of stabilized active chlorine is formed from urea and elemental chlorine, comprising the formation of chlorourea. Said chlorourea is contacted with a bromide source, providing bromourea. Alternatively, the bromourea may be formed from an aqueous solution of urea and bromide by adding elemental chlorine.

The process according to the invention is advantageously used for treating water with high TOC content. In a preferred use of the technique of the invention, biofouling is removed or prevented in a volume of an aqueous liquid or on a surface in contact with an aqueous liquid, wherein said volume or surface comprises irrigation pipes, industrial cooling water, waste, water, process water, and an equipment of Pulp & Paper industry. In a preferred application of the invention, said antifouling composition unclogs pierced irrigation pipes and fertilizes the irrigated plot. Said aqueous composition may further contain salts with additional fertilizing properties.

In one embodiment of the process of the invention, said step i) of providing said antifouling composition containing a halogen source and a urea derivative is a batch process, while said step ii) of diluting is separated in time from said step i). In other embodiment, said step i) is a continual procedure including simultaneously adding the components (halogen source and urea derivatives, or solutions thereof), while said steps i) and ii) occur simultaneously. In another embodiment, a chlorourea stream and an NaBr stream are mixed, for example an aqueous stream of 40 wt % NaBr, forming bromourea at site of need. In another arrangement, an aqueous stream comprising NaOCl is mixed with an aqueous stream comprising NaBr with urea.

The invention provides a process of preparing an antifouling composition comprising water, urea, and active bromine, comprising i) preparing an aqueous solution of urea having a concentration of up to 45 wt %, for example from 2 wt % to 45 wt %; ii) adding to said solution obtained in step i) an active chlorine source selected from the group consisting of $Cl_2$, TCCA, Na-DCC, and halogenated alkylhydantoins selected from BC-DMH, DC-DMH, BC-MEH, DC-MEH, and the like, at a temperature of between 0° C. and 25° C., while stirring, wherein the molar ratio urea/chlorine is greater than about 1/1 and the total chlorine amount is up to 10 wt %, preferably from 1 wt % to 7 wt %, for example 5.6 wt %, thereby obtaining an aqueous composition of stabilized active chlorine; iii) admixing to said stabilized active chlorine a bromide source (such as bromide or HBr) to an amount corresponding to a molar ratio Br/Cl of from 0.5 to 2.0, at a temperature of between 0° C. and 25° C.; and iv) optionally adding to the mixture obtained in step ii) or step iii) salts or acids (such as $H_3PO_4$) with fertilizing properties; wherein a time period between said steps ii) and iii) is up to two years. The invention relates to an antifouling composition comprising i) urea having a concentration of from 0.1 wt % to 45 wt %, for example from 2 wt % to 45 wt %; ii) an active chlorine source selected from the group consisting of $Cl_2$, TCCA, Na-DCC, and halogenated alkylhylhydantoins selected from BC-DMH DC-DMH, BC-MEH, DC-MEH and the like, where the total chlorine amount is from 1 to 5 wt %; and iii) a bromide source selected from NaBr, KBr, and HBr, where the molar ratio of Br to Cl is from 0.2 to 2.0, for example from about 0.5 wt % to about 2.0 wt %; wherein the active halogen expressed as active chlorine is at least 0.5 wt % (calculated as total chlorine). Hydantoin derivatives usually comprise alkylhydantoins, such as dimethyhydantoins (DMH), or methyethylhydantoins (MEH), which are halogenated by chlorine (for example, DC), bromine (for example, DB), or by both (BC).

DETAILED DESCRIPTION OF THE INVENTION

It has now been surprisingly found that bio-fouling, for example bio-fouling which clogs pierced irrigation pipes, can be very efficiently handled by applying antifouling compositions containing water, bromine, and urea. Also surprising was the finding that bromourea formed by the interaction of chlorourea with bromide sources exhibited better biocidal performance than chlorourea or bromourea prepared by the halogen addition to an aqueous urea. These findings led to developing one aspect of the present invention, namely an antifouling composition and an antifouling method comprising an acidic composition containing urea or a derivative thereof, an active chlorine source which is stabilized by said urea derivative, and a bromide source to be activated by said active chlorine source, thereby utilizing the superior storage stability of the urea/chlorine compositions, and the superior biocidal activity of the urea/bromine compositions.

Antifouling compositions of the invention are effective even at very low concentrations, down to several ppm of active bromine. Concentrated stock solutions (3-20 wt % chorine) can be used for prolonged storage at ambient temperatures and than diluted to desired working concentrations. Other halogen sources and urea derivatives can be used. Other urea derivatives may comprise, for example, biuret, polyurea, or thiourea. In one aspect, the invention provides a process of removing or preventing biofouling in a volume of an aqueous liquid or on a surface in contact with an aqueous liquid, comprising acidic solutions of urea-stabilized active bromine sources, the example of such solutions being aqueous mixtures of elemental bromine with urea. In the second aspect, the invention provides a process of removing or preventing biofouling in a volume of an aqueous liquid or on a surface in contact with an aqueous liquid, comprising acidic solutions of urea-stabilized active chlorine sources which activate bromide sources. In a preferred embodiment, provided is a process of removing or preventing biofouling in a volume of an aqueous liquid or on a surface in contact with an aqueous liquid, comprising a chlorourea acidic solution reacting with bromide sources (such as NaBr, KBr, $NH_4Br$, HBr, urea hydrobromide), wherein the components may be employed as pure solids or solutions. The molar ratio of urea to chlorine and also to bromine is preferably at least 1:1, and the pH of said aqueous composition is less than 4.0. Halogen sources may comprise, for example, $Br_2$, BrCl, $Cl_2$, halogenated alkylhydantoin selected from BC-DMH, DB-DMH, DC-DMH, BC-MEH, DB-MEH, DC-MEH, and the likes, TCCA, Na-DCC, a mixture of NaBr with an oxidizer, active bromine from electrolytic process, and hypochlorites. A concentration of halogen (as total halogen) may be up to 20 wt %, around 0.5-6 wt % is often useful. In a preferred process according to the invention, said halogen is preferably present in the aqueous composition in a concentration of from about 0.1 to about 20 wt % of chlorine or bromine, more preferably up to about 10 wt % of chlorine or bromine (calculated as total chlorine), for example 8 wt %, or 6 wt %, or 5 wt %, or 4 wt %, or 3 wt %, or 2 wt %. Chlorine may have, for example, a concentration of from 1 to 5 wt % (initially corresponding to active chlorine), and bromine to be activated (added to active chlorine solution in the form of bromide source) may have, for example, a concentration of from 0.1 to 2 mol/mol in regard to total chlorine. Stock solutions are stable on storage, particularly stock solutions comprising active chlorine without bromide source. The term "stable" as used herein, relating to stabilized active halogen solutions of the invention having a nominal concentration of active halogen, expressed as available chlorine c, means a solution of which active halogen concentration does not decrease below the value c on storage at ambient temperature in the dark during the specified period. A desired nominal range, according to the intended application of said aqueous composition, may comprise values selected from the group consisting of 0.1 wt %, 0.2 wt %, 0.3 wt %, 0.4 wt %, 0.5 wt %, 0.6 wt %, 0.75 wt %, 1.0 wt %, 1.5 wt %, 2 wt %, 2.5 wt %, 3.0 wt %, up to 4 wt %, and up to 10 wt %. Working solutions exhibit biocidal activity when diluted (or deactivated by storage) down to a concentration of active bromine of 0.1 ppm. Practical working solutions may, for example, comprise a bromine concentration, measured as available chlorine, according to the desired use, of about 0.5 ppm. In other applications, said concentration may be selected from the group consisting of 1 ppm. 2 ppm, 3 ppm, 5 ppm, 10 ppm, 20 ppm, 30 ppm, and 50 ppm as available chlorine or as active chlorine. Other applications may require higher concentrations. For prolonged storage, and later use according to the invention, it is advantageous to utilize more concentrated aqueous chlorine solutions (preferably up to 1-4%), which are surprisingly stable on storage even if being concentrated. In contrast to many known methods, a process according to the invention utilizes antifouling solutions which never exhibit alkali pH; on the contrary, the antifouling solutions exhibit very acidic pH. The pH is preferably lower than 4, for example lower than 3, and often lower than 2. The antifouling solutions of the invention comprising active bromine are effective also in the presence of high organic loading in the treated water; a preferred embodiment of the invention comprises the treatment of water with high TOC content, such as in the Pulp & Paper industry, or processing industrial waters, such as cooling tower water. For such applications, rather lower urea/bromine ratios can be used, for example, 1/1 or 1/2. In a preferred embodiment of the invention, antifouling treatment comprises irrigation pipes. Said antifouling composition unclogs pierced irrigation pipes, and simultaneously it fertilizes the irrigated plot.

The invention provides a process of preparing an antifouling composition consisting of water, urea derivative, and a halogen source, comprising i) preparing an aqueous solution of urea derivative; ii) adding a halogen source to said urea solution at a temperature of between the freezing temperature and about 25° C., for example between 0° and 25° C., while stirring, wherein the molar ratio urea/halogen is at least 1/4, preferably at least 1/1. Possibly, said halogen source may be added to said urea solution in the presence of NaBr. Said halogen source may be, for example, elemental bromine or chlorine, BrCl, halogenated alkylhydantoin selected from BC-DMH, DB-DMH, DC-DMH, BC-MEH, DB-MEH, DC-MEH, and the likes, etc. In a preferred embodiment, said source is elemental chlorine, to be stabilized by urea, and later to activate bromine from a bromide source, providing a stabilized and active bromine (bromourea).

The process for preparing the antifouling composition may, in one embodiment, be a continuous process comprising simultaneously adding a urea solution and a halogen solution to the treated water, for example to cooling water, wherein said halogen source comprises bromine or chlorine. Preferably, simultaneously mixed are urea, active chlorine source, and a bromide source. In other embodiment, simultaneously mixed are urea, bromide source, and an oxidizer, so creating bromo/urea in situ; the oxidizer being, for example, chlorine, chlorourea, hypochlorite, peroxide, bromate, bromine obtained by an electrolytic process, and the like; the process may comprise simultaneous dilution of the composition.

Biofouling is an undesired accumulation of organisms, such as animals or plants or fungi or bacteria, or their products or products of their decomposition in liquid volumes or on wet surfaces. Biofouling often comprises microorganisms, such as bacteria, fungi, algae, etc., and is called microfouling. Biofouling is found in almost all circumstances where water based liquids are in contact with other materials. Examples of afflicted surfaces include membranes, pipelines, and other industrial and agricultural equipments. Bio-fouling may be controlled by including biocides, by surface coatings, etc. The terms "antifouling process", as used herein, is a process of removing the accumulation or preventing the accumulation of the said organisms, particularly microorganisms, or their products or products of their decomposition in aqueous liquid volumes or on surfaces in contact with aqueous liquids. The term "antifouling composition", as used herein, denotes an aqueous solution comprising urea and halogen according to the present invention.

A major agro-technical concern is found in the application of pierced irrigation pipes due to clogging of the system. The clogging is composed of several mechanisms: (a) particulate matter—clogging and narrowing the flow path; (b) scaling—precipitating salts (e.g. carbonate, phosphate, sulfate); (c) adsorption—due to hydrophobic interactions of soluble or colloidal organic materials (e.g., humic substances, soluble microbial products, cell debris); and (d) bio-fouling—biofilm formation and algal growth. The final formation of a fouling layer in distribution lines, or the clogging of emitters is usually the concerted action of more than one type of events. Since suspended materials can be avoided, and algae growth can be controlled, the more acute form of fouling comprises in situ formation of particulate material by super-saturation (scaling), hydrophobic interaction (adsorption), and bio-fouling (biofilm). The present invention provides the means to interfere both with said bio-fouling and with said scaling—due to the acidic nature of the stabilized activated bromine; endangered or afflicted surfaces are treated with aqueous solutions of a halogen source and a urea derivative, such as bromine/urea compositions, which are relatively resistant to degradation and/or decomposition, and which retain acceptable capacity for oxidation and anti-bacterial activity, while acting also through the low pH. Where the term "halogen source" is used herein, a compound comprising oxidatively active halogen is intended throughout; where the term "urea derivative" is used herein, urea or its derivative are intended throughout. In obvious contexts, the term "halogen" stands sometimes for "active halogen". The molar ratio denoted as "1/40" has the same meaning as the ratio denoted "1:40". Said urea derivative may have a structure

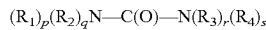

$(R_1)_p(R_2)_qN-C(O)-N(R_3)_r(R_4)_s$ wherein $R_1$, $R_2$, $R_3$, and $R_4$ are independently selected from hydrogen, alkyl, aryl, and amidoacyl having a structure $R_5CONH_2$ wherein $R_5$ represents a bond or an alkylene, and wherein $p+q=r+s=2$. An example of a halogen stabilizing compound may comprise biuret, but other compounds comprising amides or imides could be employed.

Another advantage of the present invention is the capacity of said stabilized solution to act in the presence of high TOC levels. This allows the broadening the field of the application towards media with high TOC (i.e., Pulp & Paper industry, cooling water, irrigation systems and the like). Yet another advantage of the invention is providing stabilized halogen solution, such as bromine solution, as a biocidal fertilizer—it means providing a bifunctional compound which is simultaneously a biocide and a fertilizer; the biocidal power of the halogen/urea derivative, such as bromine/urea, enables the disinfection and antifouling effect, while urea is utilized as a fertilizer—particularly in embodiments when a high urea/bromine mass ratio is used.

The stabilized halogen solution prepared according to the invention, as described herein is different from other known stabilized halogen compositions, which usually require addition of a base. The pH values of the stock solutions according to the invention are strongly acidic (for example having a pH of 3 or 2 or less), far from frequently used basic solutions exhibiting a pH as high as 11-13. The invention provides a process of preparing a stabilized aqueous halogen solution, an antifouling composition, consisting of water, urea derivative like urea itself, and a halogen source like elemental chlorine and elemental bromine; the process comprises steps of i) preparing an aqueous solution of said urea derivative; ii) adding said halogen source to said urea derivative solution at a temperature of between about 0° C. and about 25° C., while stirring, wherein the final molar ratio of urea/halogen is preferably at least 1/1, more preferably at least 2/1, still more preferably at least 3/1, for example 4/1 or more; iii) and if said halogen source comprises chlorine—converting at least a part of said active chlorine to active bromine by adding a bromide source and activating said bromide (usually by oxidizing the bromide); optionally iv) adding to the mixture salts with fertilizing and/or stabilizing properties; and optionally v) diluting the mixture with water according to the instant need. The above steps may be performed in a different order.

In urea/halogen compositions, urea will usually be in excess, the excess of urea can grow up to the limit of the urea solubility in the solution or eventually even up to the formation of a suspension with excess of urea (in a stock mixture), when beyond the solubility limit. A dilution of bromine in a urea solution will favor stabilization. The urea/bromine molar ratio may be up to 40/1, or even to 120/1.

In the method according to the invention, for controlling biofouling in a volume of an aqueous liquid or on a surface in contact with an aqueous liquid, provided is a stable aqueous antifouling composition comprising a urea derivative and a halogen source, wherein said halogen source eventually provides active bromine. The halogen source is selected from the group consisting of $Cl_{12}$, $Br_2$, BrCl, halogenated alkylhydantoin selected from BC-DMH, DB-DMH, DC-DMH, BC-MEH, DB-MEH, DC-MEH, and the likes, TCCA, Na-DCC, etc. Said halogen source or bromine may be generated in situ, for example by reacting NaBr with a hypochlorite (possibly comprising a pH of 9-10), or by electrolysis and the like, wherein the pH may be affected by such steps and eventually shifted to higher values. One of preferred halogen sources is elemental chlorine, which yields chlorourea in aqueous urea, eventually activating an added bromide to active bromine.

In a further aspect of the invention, provided is a process of removing or preventing biofouling in a volume of an aqueous liquid or on a surface in contact with an aqueous liquid, comprising preparing halogen-urea compositions by a continuous mode, by simultaneously incorporating urea and a halogen source. For example, solutions composed of urea and NaBr may be added in parallel, together with an oxidizer solution such as NaOCl solution (possibly comprising higher pH) or with other solid halogen such as TCCA, Na-DCC and halogenated DMH (acidic pH).

In one aspect of the invention, aqueous urea is employed for absorbing and stabilizing gaseous chlorine by the formation chlorourea from which bromourea is created. Bromourea may be formed also from other chlorine sources or with other oxidizers, such as sodium bromate, by their interaction with bromide sources (such as NaBr, KBr HBr, $NH_4Br$, urea hydrobromide). The presence of urea is essential in this process. It may be comprised either in the chlorine/urea complex or it may be added otherwise, possible in more portions. For example, the mixture of NaBr with an oxidizer in the presence of excess urea yields a stable solution, preferably at the molar ratio urea/Br of at least 2:1, and more preferably 3:1. Said oxidizers may, in a special aspect, comprise LiOCl, $Ca(OCl)_2$, $Cl_2O$, ozone, urea hydroperoxide, hydrogen peroxide or its precursors (percarbonates, perborates, peracetates and peroxycarboxylic acids), persulfate (oxone).

Chlorourea is one of preferred halogen sources, to be preferably converted to active bromine. Chlorourea may be prepared by introducing chlorine gas into an aqueous urea solution. Without relating the invention to any theory, it seems that during the formation of chlorourea, an equimolar amount of HCl forms, probably forming urea hydrochloride in situ. Urea hydrochloride was found useful in removing insoluble deposits on surfaces and in lowering the solids content of industrial liquids, and further in neutralizing alkaline materials in waste streams—including those generated from paper manufacturing and recycling. Urea hydrochloride is less corrosive to metal equipment and other contact surfaces than the equivalent amount of hydrochloric acid, and has a significantly less tendency to release hydrogen chloride gas. Thus, in addition to the formation of the chlorourea or bromourea, eventual urea hydrochloride may give an additional benefit in cleaning the surfaces, such as in the irrigation pipes.

Chlorourea solutions, for example having concentrations up to 5.5% of active halogen (as $Cl_2$ total) and in the presence of excess urea (1:27, 1:13 and 1:9 molar ratio), were stable for months. Chlorourea solutions were found to be more stable than bromourea solutions, both at lower and at higher temperatures. Chlorourea solutions could be stabilized with lower urea excess than bromourea, giving rise to additional applications (other than treating the irrigation pipes), such as treating industrial waters. When the biocidal activity was examined by the inventors, bromourea was found to be a better biocide than chlorourea. Consequently, a new methodology is further provided, beside directly dissolving $Br_2$ in an aqueous urea solution: bromourea is provided from the stable chlorourea solution that is mixed with bromide salts or HBr or with urea hydrobromide or other metal bromide salts (referred to as a bromide source). Bromourea can be prepared also directly from solid chlorourea, by mixing solid chlorourea with bromides. Other "solid chlorine" sources may be employed, such as halogenated alkylhydantoin selected from BC-DMH, DC-DMH, BC-MEH, DC-MEH, and the likes, TCCA, Na-DCC, to be mixed with a solution of bromide salts and urea. As said above, other oxidizers may be employed for "activating" bromides. Although bromourea is more effective than chlorourea in the biocidal uses, also chlorourea was found quite powerful, particularly at high TOC loadings, even though requiring long contact times than bromourea. The urea derivative/halogen source solutions according to the invention may comprise iodide/iodine in special applications.

The invention, thus, relates to the use of bromourea obtained from chlorourea for treating irrigation pipes. The preparation of stable bromourea solution includes introducing bromine into a urea solution whereas urea to bromine molar ratio is preferably 1:1 or higher, such as in the molar ratio of 3:1, or more preferably 4:1, or in many applications more preferably 18:1, or 40:1. In some preferred embodiments, the bromine concentration may be about 3% wt %, in others about 1%. Urea derivatives may be employed in a process according to the invention instead of urea, including glycoluryl, polyurea, thiourea, biuret, aliphatic or aromatic amides, and similar compounds. Mixing a chlorourea (the term comprises chlorinated urea or urea derivatives) with bromide sources, while ensuring the desired urea excess by eventual urea additions, provides a superior antifouling composition. Other "solid chlorine" sources, i.e. halogenated alkylhydantoin selected from BC-DMH, DC-DMH, BC-MEH, DC-MEH, and the likes, TCCA, Na-DCC may be mixed with a solution of bromide salts and urea. In a preferred embodiment, gaseous chlorine is added to a solution of urea and bromide sources. In one embodiment, bromourea solution (containing HBr) may be mixed with chlorourea solutions in order to increase the concentration of bromourea in the mixture, in other embodiment, solid chlorourea may be mixed with NaBr and urea. Usually, the presence of 3-4 molar excess of urea is important for the formation of a considerably stable bromourea.

In one embodiment, an antifouling composition comprising bromourea solution is prepared for immediate use in treated water, by mixing an aqueous stream of urea and NaBr with an aqueous stream of an oxidizer, where the urea:oxidizer molar ratio is at least 2:1, and more preferably at least 3:1 molar ratio. The urea derivatives to be employed may comprise polyurea, related amides, imides, amines, which exhibit groups susceptible to halogenation. When using a polymeric substance, it can be regenerated by passing t-BuOCl through the polymer after loss of activity.

The invention will be further described and illustrated by the following examples.

EXAMPLES

Methods

The bromine solutions were prepared by adding bromine to an aqueous solution of urea. The total active bromine was monitored by a Titroprocessor (using sodium thiosulfate as the titrating agent). The result was further confirmed with the DPD Nova instrument Kit.

Microbial experiments used the following materials:

Inoculum of bacteria (Activated sludge taken from Domestic Waste Water treatment Plant—Haifa).

R2A agar for general counting.

Tryptone, in amounts 0.025, 0.119, and 0.239 g solid tryptone respectively, was weighed and dissolved in 1 liter of buffer.

Neutralization solution ($NaHSO_4$).

Titration solution, 7.84 g of sodium $Na_2S_2O_3.5H_2O$ was dissolved in 1 liter distilled water.

Bromine-urea solution, prepared by dissolving urea 15.02 g (250.3 mmol, 15% concentration) and $Br_2$ (1.04 g, 6.53 mmol, 1.04% concentration) in 84 g $H_2O$ (urea:$Br_2$ molar ratio=38.3:1).

Erlenmeyers (250 ml).

Example 1

1.08% $Br_2$ Concentration and 15% Urea (Urea:$Br_2$=37:1 Molar Ratio)

Urea (MW 60, 15.06 g, 250 mmol) was dissolved in $H_2O$ (84.1 g) in a 150 ml dark bottle, then $Br_2$ (MW 159.8, 1.08 g, 6.76 mmol) was added to produce a yellowish solution (pH 2.2). The solution was kept at ambient temperature in the dark and was found stable for 11 days—98.16% of the original active bromine concentration. After 28 days the solution showed 91.6% of the original active bromine concentration. After 53 days the solution showed 84.1% of the original active bromine concentration.

Example 2

1.05% $Br_2$ Concentration and 46% Urea
(Urea:$Br_2$=105.9:1 Molar Ratio)

Urea (MW 60, 46 g, 766.8 mmol) was dissolved in $H_2O$ (53 g) in a 150 ml dark bottle, then $Br_2$ (MW 159.8, 1.06 g, 6.6 mmol) was added to produce a yellowish solution (pH 2.7). The solution was kept at ambient temperature in the dark and was found stable for 6 days—no change was found for the measured active bromine as compared with the original active bromine concentration.

Example 3

1.03% $Br_2$ Concentration and 7.56% Urea
(Urea:$Br_2$=19.5:1 Molar Ratio)

Urea (MW 60, 7.6 g, 126 mmol) was dissolved in $H_2O$ (91.5 g) in a 150 ml dark bottle, then $Br_2$ (MW 159.8, 1.03 g, 6.48 mmol) was added to produce a yellowish solution (pH 2). The solution was kept at ambient temperature in the dark and was found stable for 11 days—96.1% of the original active bromine concentration. After 28 days the solution showed 91.3% of the original active bromine concentration.

Example 4

1.09% $Br_2$ Concentration and 3.78% Urea
(Urea:$Br_2$=9.23:1 Molar Ratio)

Urea (MW 60, 3.78 g, 63.1 mmol) was dissolved in $H_2O$ (95.3 g) in a 150 ml dark bottle, then $Br_2$ (MW 159.8, 1.09 g, 6.83 mmol) was added to produce a yellowish solution (pH 1.93). The solution was kept at ambient temperature in the dark and after 11 days—89% of the original active bromine concentration was detected. After 28 days the solution retained 74.3% of the original active bromine concentration.

Example 5

3.38% $Br_2$ Concentration and 45.9% Urea
(Urea:$Br_2$=36.2:1 Molar Ratio)

Urea (MW 60, 46 g, 766.7 mmol) was dissolved in $H_2O$ (50.83 g) in a 150 ml dark bottle, then $Br_2$ (MW 159.8, 3.38 g, 21.2 mmol) was added to produce a yellowish solution (pH 2.4). The solution was kept at ambient temperature in the dark and after 5 days—98% bromine of the original active bromine concentration was detected. After 14 days 90% bromine of the original active bromine concentration was detected.

Example 6

1.04% $Br_2$ Concentration and 0.75% Urea (Urea:$Br_2$ 1.9:1 Molar Ratio)

Urea (MW 60, 0.75 g, 12.5 mmol) was dissolved in $H_2O$ (98.53 g) in a 150 ml dark bottle, then $Br_2$ (MW 159.8, 1.05 g, 6.57 mmol) was added to produce a yellowish solution (pH 1.95). The solution was kept at ambient temperature in the dark and after 1 day 96.9% active bromine of the original active bromine concentration was detected. Note: after 3 days 82.3% bromine of the original active bromine concentration was detected.

Example 7

1.1% $Br_2$ Concentration and 0.355% Urea
(Urea:$Br_2$=0.86:1 Molar Ratio)

Urea (MW 60, 0.3675 mg, 5.93 mmol) was dissolved in $H_2O$ (98.6 g) in a 150 ml dark bottle, then $Br_2$ (MW 159.8, 1.1 g, 6.9 mmol) was added to produce a yellowish solution (pH 2.02). The solution was kept at ambient temperature in the dark, and after 1 day 94.8% of the original active bromine concentration was detected. Note: after 3 days 74.6% bromine of the original active bromine concentration was detected.

Example 8

1.04% $Br_2$ Concentration and 13% Urea
(Urea:$Br_2$=33.2:1 Molar Ratio) in the Presence of Inorganic Salts (4.4% $KNO_3$, 15.6% KCl)

Urea (MW 60, 13 g, 216.95 mmol), $KNO_3$ (MW 101.1, 4.4 g, 43.56 mmol), KCl (MW 74.55, 15.57 g, 208.87 mmol) were dissolved in $H_2O$ (66 g) in a 150 ml dark bottle, then $Br_2$ (MW 159.8, 1.04 g, 6.53 mmol) was added to produce a yellowish solution (pH 1.88). The solution was kept at ambient temperature in the dark, and after 5 days the original active bromine concentration did not change. Note: after 11 days 97.1% bromine of the original active bromine concentration was detected.

Example 9

1.08% $Br_2$ Concentration and 13% Urea
(Urea:$Br_2$=32.2:1 Molar Ratio) in the Presence of an Inorganic Salt (19.9% $KNO_3$)

Urea (MW 60, 13 g, 217 mmol), $KNO_3$ (MW 101.1, 19.95 g, 197.35 mmol), were dissolved in $H_2O$ (66 g) in a 150 ml dark bottle, then $Br_2$ (MW 159.8, 1.08 g, 6.74 mmol) was added to produce a yellowish solution (pH 2.44). The solution was kept at ambient temperature in the dark, and after 4 days the original active bromine concentration did not change.

Example 10

1.09% $Br_2$ Concentration and 13% Urea
(Urea:$Br_2$=31.7:1 Molar Ratio) in the Presence of an Inorganic Salt (19.9% KCl)

Urea (MW 60, 13 g, 216.7 mmol), KCl (MW 74.55, 20 g, 268.13 mmol), were dissolved in $H_2O$ (66 g) in a 150 ml dark bottle, then $Br_2$ (MW 159.8, 1.09 g, 6.83 mmol) was added to produce a yellowish solution (pH 2.2). The solution was kept at ambient temperature in the dark, and after 4 days the original active bromine concentration did not change.

Example 11

1% Br$_2$ Concentration and 13.3% Urea (Urea:Br$_2$=35.3:1 Molar Ratio) in the Presence of Inorganic Salt (4% KNO$_3$, 5% KCl and 8.7% KH$_2$PO$_4$)

Urea (MW 60, 13.3 g, 221.56 mmol), KNO$_3$ (MW 101.1, 4.02 g, 39.74 mmol), KCl (MW 74.55, 5 g, 67.14 mmol) and KH$_2$PO4 (MW 136.09, 8.7 g, 63.96 mmol) were dissolved in H$_2$O (68 g) in a 150 ml dark bottle, then Br$_2$ (MW 159.8, 1 g, 6.27 mmol) was added to produce a yellowish solution (pH 2.9). The solution was kept at ambient temperature in the dark, and after 5 days the original active bromine concentration did not change.

Example 12

Microbial Efficacy of Different Concentrations of the Bromine/Urea Composition Under Different TOC Loading The biocidal efficacy of the antifouling composition at different organic loads of 0, 5, 50 and 100 ppm TOC, was examined under different biocidal concentrations (1, 2.5, and 5 ppm) at pH 7.
1) 1 ml of inoculum was added to tryptone solutions (placed in 3 erlenmeyers, 100 ml each, with different concentrations of TOC-0, 10, 50 and 100 ppm).
2) 1 ml of each sample was inoculated on R2A agar (pour plate method). The result stands for the bacteria count at zero time.
3) For each of the tryptone concentrations (0, 10, 50, 100 ppm TOC) an inoculum of bacteria (1 ml) and the appropriate biocide concentration were added.
4) After 30 min. of shaking (100 rpm), 1 ml of each sample was transferred to a tube filled with 9 ml of the neutralization solution. An aliquot of 1 ml was taken from this solution and added to another tube containing 9 ml of buffer solution. The solution was mixed under vortex. This operation was repeated for 4 more times.
5) 1 ml from the two lowest dilutions was inoculated on a R2A agar (by the pour plate method).
6) After the plates were incubated at 25° C. for 5-7 days, the bacteria count was recorded.
The results are presented in Table 1.

TABLE 1

Bromine - urea compositions and % kill at different TOC concentrations

| TOC conc. (ppm) | Biocide conc. (ppm as Cl$_2$) | | |
|---|---|---|---|
| | 1 | 2.5 | 5 |
| 0 | 99.55 | 99.8 | 99.84 |
| 10 | 52.42 | 97.53 | 99.78 |
| 50 | 4.84 | 30.61 | 90.3 |
| 100 | 0 | 14.15 | 55.5 |

Example 13

Other Biocides

Additional experiments were carried out to compare the activity of other biocides: NaBr activated with NaOCl creating NaOBr solution.

The results are given in Tables 2-3, respectively.

TABLE 2

Activated NaBr* compositions and % kill at different TOC concentrations

| TOC conc. (ppm) | Biocide conc. (ppm as Cl$_2$) | | |
|---|---|---|---|
| | 1 | 2.5 | 5 |
| 0 | 98.9 | 98 | 99.5 |
| 10 | 36.1 | 84.6 | 96.5 |
| 50 | 0 | 19.2 | 45.4 |
| 100 | 0 | 5 | 9 |

*NaBr activated with NaOCl creating NaOBr solution;

TABLE 3

NaOCl compositions and % kill at different TOC concentrations

| TOC conc. (ppm) | Biocide conc. (ppm as Cl$_2$) | | |
|---|---|---|---|
| | 1 | 2.5 | 5 |
| 0 | 54.1 | 95.5 | 99.6 |
| 10 | 3.7 | 34.6 | 97.1 |
| 50 | 0 | 12.7 | 65.9 |
| 100 | 0 | 0 | 0 |

Example 14

Biocidal Activity Against Simulated Biofilm Systems

A biofilm simulation system developed by the Biofilm Bozeman Institute Montana (Grobe, K. J, Zahller, J and Stewart P. S., 2002 in "Role of dose concentration in biocide efficacy against *Pseudomonas aeruginosa* Biofilms", J. Industrial Microbiology & Biotechnology, vol. 29, pp 10-15), was used in this experiment to evaluate the efficacy of bromine/urea against biofilm.

Preparation of the Alginate Beads:

The biofilm simulation was created by entrapping bacteria in alginate gel beads. A plate of R2A agar was streaked with *Pseudomonas aeruginosa* (ATCC 15442) and incubated at 35° C. overnight. Buffer phosphate at pH 7.2 was used to scrap off the bacteria from the agar plate and to create a suspension. The bacterial suspension was mixed with an equal volume of an aqueous 4% sodium alginate solution, to make a final 2% alginate solution. The alginate and bacterial slurry were placed in a 50 ml syringe attached to a 22 gauge needle, connected to a compressed air tank, allowing the syringe to be pressurized. At 20 psig pressure a stream of small drops was forced out and dropped into a stirred solution of 50 mM CaCl$_2$. The Ca$^{+2}$ cross linked the alginate, and semi solid beads with entrapped bacterial cells were formed. The beads were allowed to stir in the CaCl$_2$ solution for about 20 minutes, and then rinsed in a dilute 5 mM CaCl$_2$ solution. Several flasks containing 100 beads each were incubated overnight at 35° C. on a rotating shaker in a buffer solution (at pH 7) with 5 mM addition of CaCl$_2$ to maintain the beads structure. The resulting beads diameter is about 2 mm.

General Description of the Experiment:

At the beginning of the experiment, the supernatant of the beads buffer suspension containing 5 mM CaCl$_2$ was decanted and replaced by the 100 ml biocide solution with the required concentration (Urea-bromine compositions prepared by dissolving urea 15.02 g (250.3 mmol, 15% concentration) and 1.17 g Br$_2$ (7.32 mmol, 1.17% concentration) in 84 g H$_2$O (34.2:1 urea:Br$_2$ molar ratio). After different interval contact times, 10 beads were removed and placed in a 5 g/l sodium thiosulfate solution containing 50 mM sodium citrate. The sodium citrate was used to dissolve the alginate gel and release the bacteria into the solution. The neutralizer-citrate solution was placed in the refrigerator for 2 hours, than diluted and placed on R2A agar plates using pour plate technique. The plates were incubated at 35° C. for 24-48 hours and counted. The efficacy and toxicity of the neutralizer were checked as well as a control experiment without biocide addition. Four concentrations (0.5, 1, 2.5 and 5 ppm) were tested at four different contact times (5, 15, 30, and 60 min). Table 4 describes the surviving colony forming units (CFU) of the bacteria after the biocide treatment at different contact times.

TABLE 4

Biocidal efficacy of a bromine urea composition against bacterial beads (survival of bacteria (CFU) as a function of biocide loading and contact time

| Contact Time | Biocide concentration (ppm as Cl$_2$) | | | |
|---|---|---|---|---|
| | 0.5 | 1 | 2.5 | 5 |
| 0 | 6.00E+06 | 6.00E+06 | 6.00E+06 | 6.00E+06 |
| 5 | 5.45E+06 | 6.00E+06 | 2.15E+06 | 1.63E+05 |
| 15 | 4.85E+06 | 2.13E+06 | 1.30E+04 | 1.00E+00 |
| 30 | 4.10E+06 | 4.35E+05 | 1.00E+00 | 1.00E+00 |
| 60 | 1.45E+06 | 2.30E+04 | 1.00E+00 | 1.00E+00 |

The bacterial concentration count was reduced by 0.5 logs at a biocide concentration of 0.5 ppm, and by 2 logs at a biocide concentration of 1 ppm, after 60 minutes of contact time. After the same contact time, 7 logs of the bacterial counts were reduced (100% kill), with the 2.5 and 5 ppm concentrations (as Cl$_2$), after 15 and 30 minutes, respectively.

Example 15

Preparation of Chlorourea in the Presence of Urea (1.84% as Cl$_2$ Total, Urea 45 wt %, 1:30 Molar Ratio)

Urea (46.1 g, 767.9 mmol) was dissolved in H$_2$O (54.9 g) in a 250 ml three neck flask, then gaseous Cl2 (1.8 g, 25.5 mmol) was added during 2 min. (exothermic) to produce a colorless solution, with a pH of −1.56 and 1.84% chlorine as total Cl$_2$. The solution was stable during 6.6 months as 100% of the original total Cl$_2$ was detected (iodometry), which decreased to 98.3% after 8.2 months. UV: 244 nm.

Example 16

Preparation of Chlorourea in the Presence of Urea (4% as Cl$_2$ Total, 43.6% wt % Urea (1:13 Molar Ratio)

Urea (46 g, 767.4 mmol) was dissolved in H$_2$O (55.4 g) in a 250 ml three neck flask, then gaseous Cl$_2$ (4.2 g, 59.4 mmol) was added during 3 min. (exothermic) to produce a colorless solution with a pH 1.13, and 4% Cl$_2$ (total). The solution was stable during 5.5 months as 100% of the original total Cl$_2$ was detected, which decreased to 99% after 7.25 months and to 95.5% after 8.2 months.

Example 17

Preparation of Chlorourea in the Presence of Urea (1.9% as Cl$_2$ Total, Urea 14.8 wt %, 1:9.2 Molar Ratio)

Urea (15.1 g, 251 mmol) was dissolved in H$_2$O (85.2 g) in a 250 ml three neck flask, then gaseous Cl$_2$ (1.94 g, 27.4 mmol) was added during 1 min. (exothermic) to produce a colorless solution with a pH −1.11 and 1.9% as total Cl$_2$. The solution showed 98.7 of the expected total Cl$_2$ (total) after 5.5 months which decreased to 91.2% after 8.2 months.

Example 18

Preparation of Chlorourea in the Presence of Urea (0.64% as Cl$_2$ Total, Urea 15 wt %, 1:27 Molar Ratio)

Urea (15 g, 250.9 mmol) was dissolved in H$_2$O (85.25 g) in a 250 ml three neck flask, then gaseous Cl$_2$ (0.64 g, 9.11 mmol) was added during 50 sec. (exothermic) to produce a colorless solution with a pH 1.38 and 0.64% Cl$_2$ (total). After 6.6 months the solution showed 100% of the original total chlorine.

Example 19

Preparation of Chlorourea in the Presence of Urea (5.5% as Cl$_2$ Total, Urea 43.7 wt %, 1:9.2 Molar Ratio)

Urea (46 g, 766.7 mmol) was dissolved in H$_2$O (53.4 g) in a 250 ml three neck flask, then gaseous Cl$_2$ (5.9 g, 83.3 mmol) was added during 4 min. (exothermic) to produce a colorless solution, with a pH of −0.82 and 5.5% Cl$_2$ (total). After 3 months 100% of the original total Cl$_2$ was detected, which decreased to 99.2% of the original concentration after 4.3 months, 97.8% after 5.3 months and 90.75% after 8 months.

Example 20

Preparation of Chlorourea in the Presence of Urea (2.1% as Cl$_2$ Total, Urea 44.5 wt %, 1:27 Molar Ratio)

Urea (46.1 g, 768.4 mol) was dissolved in H$_2$O (53.3 g) in a 250 ml three neck flask, then gaseous Cl$_2$ (2 g, 28.6 mmol) was added during 5 min. (exothermic) to produce a colorless solution, with a pH of −1.50 and 2.1% as total Cl$_2$. After 3.8 days 100% of the original total Cl$_2$ was detected.

Example 21

Preparation of Chlorourea in the Presence of Urea (4% as Cl$_2$ Total, Urea 44.6 wt %, 1:13 Molar Ratio)

Urea (46 g, 767.7 mmol) was dissolved in H$_2$O (53 g) in a 250 ml three neck flask, then gaseous Cl$_2$ (4.17 g, 58.8 mmol) was added during 6 min. (exothermic) to produce a colorless solution, with a pH of −1.07 and 4% as total Cl$_2$. After 5.25 months 100% of the original total $Cl_2$ was detected which decreased to 99.7% after 6.4 months, and to 97.18% after 8 months.

Example 22

Preparation of Chlorourea (3.24% as $Cl_2$ Total) in the Presence of Urea, 1:0.88 Molar Ratio This example shows the preparation of chlorourea in the presence of low excess of urea. To an aqueous solution of urea (2.54 g, 42.3 mmol, dissolved in $H_2O$ (94.5 g)) in a 250 ml three neck flask was added gaseous $Cl_2$ (g) (3.4 g, 47.8 mmol) during 13 min. (exothermic) to produce a colorless solution with 3.24% as total chlorine (95.6% of the calculated amount. After 18.5 hours, 63.5% of the original total $Cl_2$ was detected which decreased further to 39.9% after 2.9 days.

Example 23

Preparation of Chlorourea (3.5%, as $Cl_2$ Total) in the Presence of Urea (1:1.75 Molar Ratio)

Urea (5.1 g, 84.7 mmol) was dissolved in $H_2O$ (94.5 g) in a 250 ml three neck flask, then gaseous $Cl_2$ (3.44 g, 48.5 mmol) was added during 16 min. to produce a colorless solution with a pH −0.07, retaining 3.48% as chlorine total. After 20.6 hours, 97% of the original total $Cl_2$ was detected which decreased further to 51.3% after 21 days.

Example 24

Preparation of Chlorourea (3.15% as $Cl_2$ total) in the Presence of Urea. (1:1.4 Molar Ratio)

Urea (3.8 g, 63.5 mmol) was dissolved in $H_2O$ (93.2 g) in a 250 ml three neck flask, then gaseous $Cl_2$ (3.2 g; 45 mmol) was added during 13 min. to produce a colorless solution with a pH 0.15 and 3.48% as chlorine total (UV, 245 nm). After 21 hours, 90.74% of the original total $Cl_2$ was detected which decreased further to 41.4% after 17 days.

Example 25

Preparation of Chlorourea (3.16% as $Cl_2$ Total) in the Presence of Urea (1:4.8 Molar Ratio)

Urea (12.7 g, 211.5 mmol) was dissolved in $H_2O$ (84.3 g) in a 250 ml three neck flask then gaseous $Cl_2$ (3.1 g, 43.72 mmol) was added during 12 min. (exothermic) to produce a colorless solution, with a pH of −0.38, and 3.16% as total $Cl_2$. after 3 months days 96.6% of the original total $Cl_2$ was detected, that decreased to 85.2% after 5 months.

Example 26

Preparation of Chlorourea (2.97% as $Cl_2$ Total) in the Presence of Urea. (1:3 Molar Ratio)

Urea (7.6 g, 127 mmol) was dissolved in $H_2O$ (93.2 g) in a 250 ml three neck flask, then gaseous $Cl_2$ (3 g, 42.6 mmol) was added during 10 min. (exothermic) to produce a colorless solution with a pH 0.29, retaining 2.97% as total $Cl_2$. After 39 days the solution showed 87.1% of the original total chlorine that decreased to 81% after 2.1 months, and to 58% after 4 months.

Example 27

Preparation of Chlorourea (3% as $Cl_2$ Total) in the Presence of Urea (1:4 Molar Ratio)

Urea (10.2 g, 169.3 mmol) was dissolved in $H_2O$ (86.9 g) in a 250 ml three neck flask then gaseous $Cl_2$ (3 g, 42.3 mmol) was added during 12 min. (exothermic) to produce a colorless solution with a pH −0.19, retaining 3% as total $Cl_2$. After 39 days the solution showed 96.65% of the original total chlorine that decreased to 95% after 2.1 months and to 78.5% after 4 months.

Example 28

Preparation of Chlorourea (4% as $Cl_2$ Total) in the Presence of Urea (1:4 Molar Ratio)

Urea (13.55 g, 225.8 mmol) was dissolved in $H_2O$ (82.5 g) in a 250 ml three neck flask, then gaseous $Cl_2$ (4 g, 56.55 mmol) was added during 6 min. to produce a colorless solution with a pH of 0.82, retaining 4% as $Cl_2$ (total). After 13 days the solution showed 99.1% of the original total chlorine concentration, which decreased to 93.8% after 2.1 months and to 84.55% after 3 months.

Example 29

Preparation of Chlorourea (4.16% as $Cl_2$ Total) in the Presence of Urea (1:2.9 Molar Ratio)

Urea (10.2 g, 169.3 mmol) was dissolved in $H_2O$ (85.9 g) in a 250 ml three neck flask, then gaseous $Cl_2$ (4.15 g, 58.5 mmol) was added during 6 min. to produce a colorless solution with a pH of −0.52, retaining 4.16% as $Cl_2$ (total). After 6 days the solution showed 97% of the original total chlorine concentration which decreased to 94.9%, after 13 days, to 85% after 26 days and to 67.8% after 2.1 months and to 58.4% after 3 months.

Example 30

Preparation of Bromourea from Chlorourea and NaBr (1:2 Molar Ratio)

In a 250 ml three neck flask 189.8 g of 1.57% chlorourea solution as $Cl_2$ (3 g $Cl_2$ 42 mmol, urea 45.9 wt %, 92 g, 1.53 mol) was added followed by the addition of solid NaBr (8.64 g, MW 102.89, 84 mmol) during 5 min. A yellowish solution was formed with 3.38% $Br_2$ (total). After 17 days 95.9% of the original active bromine concentration was found which decreased to 80.8% after 49 days.

Example 31

Preparation of Bromourea from Chlorourea and NaBr (1:1 Molar Ratio)

In a dark bottle equipped with a magnetic stirring bar a solution of 95.35 g of a 1.6% chlorourea solution as $Cl_2$ total (1.37 g $Cl_{12}$, 19.4 mmol $Cl_2$, urea 45.9 wt %, 43.76 g, 0.729 mol; 1:38 molar ratio) was introduced, followed by the addition of solid NaBr (2.007 mg, MW 102.89, 19.5 mmol) during 1 min. A yellowish solution with a pH of 2.01 was formed (3.18% as total bromine). After 8 days 99.06% of the active bromine was found.

Example 32

Preparation of Bromourea from Chlorourea and NaBr (1:0.5 Molar Ratio)

In a dark bottle equipped with a magnetic stirring bar, 180.9 g of a 1.44% chlorourea solution (as $Cl_2$ total) (2.6 g $Cl_{12}$, 36.7 mmol, urea 46 wt %, 83.2 g, 1.39 mol, 1:38) was introduced, followed by the addition of solid NaBr (1.9 g, MW 102.9, 18.46 mmol) during 2 min. A yellowish solution was obtained with a pH 2.03 (3.2% as total bromine, UV 272 nm (as for bromourea). After 10 days 99.7% of the original active bromine concentration was found.

Example 33

Preparation of Bromourea from Chlorourea and Aq. 48% HBr (1:2 Molar Ratio)

In a dark bottle equipped with a magnetic stirring bar, 10.2 g of a chlorourea solution (1.42% as $Cl_2$ total) (containing 0.14 g $Cl_2$, 2.04 mmol; urea 46 wt %, 4.68 g, 78 mmol, 1:38 molar ratio) was introduced, followed by the addition of 0.68 g of a 48% aq. HBr (0.33 g as HBr, MW 80.92, 4.04 mmol) during 2 min. A yellowish solution was obtained with a pH 1.48 (3% as total bromine, UV 272 nm. After 12 days 94% of the original active bromine concentration was found.

Example 34

Preparation of Bromourea from Chlorourea and Aq. 48% HBr (1:1 Molar Ratio)

In a dark bottle equipped with a magnetic stirring bar, 99.9 g of a 1.44% chlorourea solution as Cl2 total (1.44 g $Cl_2$, 20.28 mmol, urea 46 wt %, 45.9 g, 765.6 mmol, 1:38 molar ratio) was introduced, followed by the addition of 3.42 g of a 48% aq. HBr (1.64 g as HBr, 20.275 mmol) during 2 min. A yellowish solution with 3.1% as total bromine was obtained with pH 1.55. (UV 272 nm) After 12 days 97.6% of the original active bromine concentration was found.

Example 35

Preparation of Bromourea from Chlorourea and Aq. 48% HBr (1:0.5 Molar Ratio)

In a dark bottle equipped with a magnetic stirring bar, 98.5 g of a 1.44% chlorourea solution as $Cl_2$ total (1.4 g $Cl_2$, 20 mmol, urea 46 wt %, 45.3 g, 755 mmol, 1:38 molar ratio) was introduced, followed by the addition of 1694 mg of a 48% aq. HBr (813 mg as HBr, MW 80.92, 10.05 mmol) during 2 min. (exothermic) A yellowish solution was obtained with a pH 1.55 and with 3.2% as total bromine (UV 272 nm). After 12 days 99.4% of the original active bromine concentration was found.

Example 36

Preparation of Bromourea from Chlorourea and KBr (1:2 Molar Ratio)

In a 250 ml three neck flask equipped with a magnetic stirring bar, 202.8 g of 1.42% chlorourea solution as $Cl_2$ total (2.88 g $Cl_2$, 40.6 mmol, urea 46 wt %, 93.3 g, 1.55 mol, 1:38 molar ratio) was introduced, followed by the addition of solid KBr (9.7 g 81.7 mmol, MW 119.01) during 5 min. A yellowish solution was obtained with a pH 1.79 and 3.07% as total bromine. After 26 days 92.8% of the original active bromine concentration was found.

Example 37

Preparation of Bromourea from Chlorourea and KBr (1:1 Molar Ratio)

In a 250 ml three neck flask equipped with a magnetic stirring bar, 198.4 g of 1.42% chlorourea solution, as $Cl_2$ total (2.82 g $Cl_2$, 39.74 mmol, urea 46 wt %, 91.3 g, 1.52 mol, 1:38 molar ratio) was introduced, followed by the addition of solid KBr (4.75 g, 40 mmol) during 6 min. A yellowish solution was obtained with a pH 1.64 and 3.16% as total bromine. After 24 days 97.5% of the original active bromine concentration was found.

Example 38

Preparation of Bromourea from Chlorourea and NaBr (1:2 Molar Ratio)

In a 250 ml three neck flask equipped with a magnetic stirring bar, 100.1 g of 3% chlorourea solution (3 g $Cl_2$, 42 mmol, urea 15 wt %, 15 g, 0.25 mol, 1:6 mol ratio) was introduced, followed by the addition of solid NaBr (8.54 g, MW 102.89, 83 mmol) during 10 min. A yellowish solution was obtained with a pH 1.64 and 5.76% as total bromine. After 2 days 92.1% of the original active bromine concentration was found, which decreased further to 83.3% after 8 days, 75.2% after 12 days and 67.7% after 27 days (UV 268 nm).

Example 39

Preparation of Bromourea from Chlorourea and NaBr (1:2 Molar Ratio)

Into a 250 ml three neck flask equipped with a magnetic stirring bar, 100.1 g of 3.13% chlorourea solution, as $Cl_2$, (3.13 g $Cl_2$, 44.18 mmol, urea 46 wt %, 46 g, 767 mmol, 1:17 molar ratio) was added dropwise during 10 min. to NaBr solution (9.06 g, 88 mmol dissolved in 100 g $H_2O$). A yellowish solution was obtained with a pH 1.64 and 3.52% as total $Br_2$. After 15.1 days 91.7.1% of the original active bromine concentration was detected which decreased after 39 days, to 80.6%.

Example 40

Preparation of Bromourea from Chlorourea and NaBr Solution (1:2 Molar Ratio)

Into a 250 ml three neck flask equipped with a magnetic stirring bar, 100 g of 1.04% chlorourea solution, as $Cl_2$ total, (1.16 g $Cl_2$, 16.36 mmol, urea 17%wt, 17 g, 284.4 mmol, 1:17 molar ratio) was added followed by the dropwise addition (during 10 min.) of an NaBr solution (3.6 g in 96.4 g $H_2O$ g, 35.18 mmol). A yellowish solution was obtained with 1.23% as total $Br_2$). After 6.8 days 92.7% of the original active bromine concentration, dropping to 75.6% after 39 days.

Example 41

Preparation of Bromourea from BCDMH (Bromochloroalkylhydantoin selected from BC-DMH, DB-DMH, DC-DMH, BC-MEH, DB-MEH, DC-MEH, and the like) and KBr Halobrom (201 mg, 0.83 mmol, MW 242.42) was dissolved in 97.7 g $H_2O$, then urea (2.22 g, 37.02 mmol) and KBr (110.3 mg, MW 119.01, 0.93 mmol) were added (Urea:KBr 40:1 molar ratio). A light yellowish solution pH 4.79 was obtained, with 0.25% as Br2 (total). It was found stable for 50 days showing 100% of the original active bromine concentration (pH dropped to 3.86). After 4.9 months 96% of the original active bromine concentration was detected (pH 3.49). LTV (250 ppm): 275 nm.

Example 42

Preparation of Bromourea from TCCA

Into a solution of KBr (1.84 g, MW 119.01, 15.46 mmol) in $H_2O$ (51 g) in a 250 ml three neck flask was added urea (46 g, 767 mmol) and TCCA (607.2 mg MW 232.41, 2.6 mmol). A yellow solution with pH-3.84 was obtained with 1.08% as $Br_2$ (total). After 17 days the solution showed 91.6% of the original active bromine concentration, decreasing only to 88.9% after 23 days (UV, 277 nm as for bromourea), to 73% after 42 days and to 60.2% after 56 days.

Example 43

Preparation of Bromourea from Na-DCC

Into a solution of KBr (2.4 g MW 119.01, 20.06 mmol) in $H_2O$ (49 g) in a 250 ml three neck flask was added Urea (46 g, 767.12 mmol) followed by the addition of Na-DCC.$2H_2O$ (2.57 g, 10 mmol, MW 256). A solution with pH-3.84 was obtained and 2.56% as $Br_2$ (total). After 4 days the solution showed 76.6% of the original active bromine concentration.

Example 44

Preparation of Bromourea by a Parallel Addition of a Chlorourea (1.52 as $Cl_2$, 46 wt % urea) and NaBr 40% (1:1 Molar Ratio)

50.1 g of a solution of chlorourea (1.52% as Cl2 total, urea wt % 46%—0.76 g Cl2 10.7 mmol, 23 g urea, 383 mmol, 1:36 molar ratio) and 2.77 g solution of aqueous 40% NaBr (1.108 g, 10.8 mmol) were added simultaneously in such a rate as to have an addition as 1:1 molar ratio of chlorourea to NaBr during 15 min. to give a yellowish solution (pH 2.15). 98.78% of the original active Br2 was observed after 4 days (pH 2.13).

UV (250 ppm): 275 nm (bromourea).

Example 45

Preparation of Solid Chlorourea

1. Preparation of t-Butylhypochlorite [Organic Syntheses. Coll. Vol. 5, p. 184 (1973); Vol. 49, p. 9 (1969).]

In a 1-l. jacketed reactor (protected from light) equipped with a mechanical stirrer was added 500 ml. (539.45 g) of sodium hypochlorite solution (5.25%, d=~1.097, MW 74.44). The solution was cooled (<10° C.) and a solution of t-butyl alcohol (37 ml, 28.69 g, 0.387 mole, d=0.775, MW 74.12) and glacial acetic acid (24.5 ml, 0.43 mole) was added dropwise during 9 min. while the temperature was maintained below 20° C. Stirring was allowed for an additional 5 min. The lower aqueous layer is discarded, and the oily yellow organic layer is washed first with 2×50-ml. of 10% aqueous sodium carbonate and then with 50 ml. of water. The oily product is dried over 2 g. of calcium chloride and filtered to get the product 27.8 g.

2. Preparation of Solid Chlorourea [S. S. Israelstam, J. S. African Chem. Inst. 18956, 9, 30; J. S. Chaltsy S. S, Israelstam, Chem. Ind 1954, 1452]

A solution of urea (1.55 g, 25.8 mmol) in 10 ml dry MeOH (0.05% water) was cooled at 0° C., and t-butyl hypochlorite (3 ml) was added dropwise during 5 min. Stirring was allowed for an additional 15 min. The solvents were evaporated under vacuum under cooling (15° C.). 2.3 g of N-chlorourea (MW 94.5) was obtained (m.p. 75.9-76.7° C., UV 244 nm).

Example 46

Preparation of Bromourea from Solid Chlorourea and NaBr

Chlorourea (1.5 g, MW 94.5, 15.9 mmol) was dissolved in 32.3 g $H_2O$ in a 150 ml dark bottle. Then solid NaBr (1.15 g, MW 102.8, 11.2 mmol—$Cl_2$:NaBr=1:1 molar ratio) was added to produce an orange solution (pH 2.08). After 40 min 81.85% of the original active $Br_2$ (total) was detected, which decreased further to 53.2% after 18.2 hours (pH 1.67). The UV (at 250 ppm) showed an absorption at 261-264 nm.

Example 47

Preparation of Bromourea from Solid Chlorourea and NaBr and Urea (1:1:1 Molar Ratio)

NaBr 1.05 g (10.2 mmol) and urea (0.61 g, 10.2 mmol) were dissolved in $H_2O$ (47.4 g) in a 150 ml dark bottle (pH 7.55). Then solid chlorourea 97% (1 g, 10.5 mmol, 94.5) was added to produce a yellowish solution (pH 3.5) with 1.43% $Cl_2$ (total). After 69 min. 91.3% of the original active $Br_2$ (total) was detected. (pH 2.34) which decreased to 81% after 2.5 hours (pH 2.16).

UV (250 ppm): 262-265 nm.

Example 48

Preparation of Bromourea from Solid Chlorourea, NaBr and Urea (1:1:2)

NaBr (0.53 g, 5.1 mmol) and urea (0.61 g, 10.16 mmol) were dissolved in $H_2O$ (23.4 g) in a 150 ml dark bottle (pH 8.64). Then solid chlorourea (0.5 g, 5.25 mmol) was added to produce a yellowish solution (pH 3.4) with 1.48% as Cl2 (total). After 70 min. 94.3% of the original active Br2 was observed (pH 2.57) which decreased to 87.5% after 2.4 hours (pH 2.33). UV (250 ppm): 271 nm (bromourea), after 16 min. (changed to 266 nm after 79 min.)

Example 49

Preparation of Bromourea from Solid Chlorourea and NaBr and Urea (1:1:3)

NaBr (0.2 g, 1.92 mmol) and urea (0.35 g, 5.77 mmol) were dissolved in $H_2O$ (8.7 g) in a 50 ml dark bottle. Then, solid chlorourea (MW 94.5, 0.19 g, 1.98 mmol was added to produce a yellowish solution (pH 3.95) with 1.47% as Cl2 (total). After 78 min 96.1% of the expected total Br2 was found which decreased to 92.45% after 3.4 hours and to 66.5% after 20.4 hrs. UV (250 ppm): 271-273 nm (bromourea) after 15 min. (stable for 20.4 hours).

Example 50

Preparation of Bromourea from Gaseous Chlorine (1.77% as $Cl_2$) in a Solution of Urea 46 wt % and NaBr (1:1 Molar Ratio)

Urea (46 g, 766.8 mmol) and NaBr (2.22 g, 21.6 mmol) were dissolved in $H_2O$ (50.3 g) in a 250 ml three neck flask, pH 10.55). Then $Cl_2$ (1.77 g, 24.9.6 mmol) was added during 3.5 min. to give a yellowish solution with pH 1.93 and 1.77% $Cl_2$ (total), UV (250 ppm) 272 nm.

Example 51

Preparation of Bromourea from Sodium Hypochlorite and Sodium Bromide in the Presence of Urea (NaBr:Urea 1:2 Molar Ratio)

Solution A: A diluted solution of NaOCl, 1133 ppm as $Cl_2$, was prepared from a commercial aq. 13% NaOCl. Solution B: Urea (194 mg, 3.23 mmol) and NaBr (166.5 mg, 1.62 mmol) were added to a measuring flask of 100 ml filled with water. 25 ml of solution A was added to solution B. the solution was monitored by UV (272 nm).

Example 52

Preparation of Bromourea from Sodium Hypochlorite and Sodium Bromide in the Presence of Urea (NaBr:Urea, 1:3 Molar Ratio)

Solution A: A diluted solution of NaOCl, 1038 ppm as $Cl_{12}$, was prepared from a commercial aq. 13% NaOCl. Solution B: Urea (281.2 mg, 4.7 mmol) and NaBr (1631 mg, 1.58 mmol) were added to a measuring flask of 100 ml filled with water. 25 ml of solution A was added to solution B. the solution was monitored by UV (272 nm).

Example 53

Preparation of Bromourea from Sodium Hypochlorite and Sodium Bromide in the Presence of Urea (NaBr:Urea, 1:4 Molar Ratio)

Solution A: A diluted solution of NaOCl, 1106 ppm as $Cl_2$, was prepared from a commercial aq. 13% NaOCl. Solution B: Urea (377.5 mg, 6.3 mmol) and NaBr (163.4 mg, 1.59 mmol) were added to a measuring flask of 100 ml filled with water. 25 ml of solution A was added to solution B (pH 8.96). The solution was monitored by UV (272 nm).

Example 54

Preparation of Bromourea by the Oxidation of a Mixture of NaBr and Aq. HBr (48%) with Sodium Bromate in the Presence of Urea (2.06/30.67 $Br_2$/Urea)

Urea (34.95 g, 582.5 mmol) and NaBr (1008 mg, 9.8 mmol) and $NaBrO_3$ (741 mg, MW 150.89, 4.91 mmol) were dissolved in $H_2O$ (74.8) in a 250 ml three neck flask, (pH 10.43). Then HBr 48% solution (2.5 g, MW 80.9, 14.7 mmol) was added during 5 min to produce a yellowish solution retaining with 2.07% $Br_2$ as total with a pH 2.06. After 27 hours, 98.55% of the original active $Br_2$ (total) was observed (pH 2.77) which decreased to 86.9% after 5.9 days (pH 3), and to 80.6% after 9 days (pH 2.98) and to 67.15% after 13.9 days (pH 2.91).

Example 55

Preparation of Bromourea from, Sodiumbromate and Aq. 48% HBr in the Presence of Urea (2.06/30.7 $Br_2$/Urea) in the Presence of Urea Urea (35 g, 583.1 mmol) and $NaBrO_3$ (751 mg, 5 mmol) were dissolved in $H_2O$ (75.9) in a 250 ml three neck flask (pH 10.51). Then 2.46 g of aq. 48% HBr solution (14.6 mmol HBr, MW 80.92) was added during 3 min to produce a yellowish solution with 2.05% $Br_2$ (total) with pH 2.08. After 1.91 day—99.5% of the original active $Br_2$ was observed with pH 2.79, which decreased to 94.6% after 5 days (pH 3.02), to 93.2% after 6.09 days, to 88.8% after 8 days (pH 2.95) and to 77.6% after 13 days (pH 2.95).

Example 56

Preparation of Bromourea from Sodiumbromate and Aq. 48% HBr in the Presence of Urea (2.06/30.7 $Br_2$/Urea)

Urea (35 g, 583.1 mmol) and $NaBrO_3$ (733.8 mg, 4.863 mmol) were dissolved in $H_2O$ (75.3) in a 250 ml three neck flask (pH 10.61). Then 4.1 g aq. 48% HBr solution (24.4 mmol HBr) was added during 3 min to produce a yellowish solution retaining with 1.96% $Br_2$ (total) with pH 1.76. The solution was stable for 2 days, as 100% of the original active $Br_2$ was observed (pH 2.13). This decreased to 98.5% after 5 days (pH 2.22), to 97.45% after 6.1 days, to 93.9% after 8 days (pH 2.21) and to 84.7% after 13 days (pH 2.34).

Example 57

Preparation of Bromourea from Sodiumbromate, Sodiumbromide and Aq. 48% HBr in the Presence of Urea (2.06/30.6 $Br_2$/Urea)

Urea (35 g, 582.5 mmol) and NaBr (1011 mg, 9.8 mmol) and $NaBrO_3$ (734.5 mg, 4.9 mmol) were dissolved in $H_2O$ (74.6) in a 250 ml three neck flask (pH 10.40). Then 2.9 g of aq. 48% HBr solution (17.2 mmol HBr) was added during 5 min to produce a yellowish solution retaining with 2.03% $Br_2$ (total) with pH 1.8. 98.5% of the original active $Br_2$ (total) was observed after 22 hours (pH 2.57) which decreased to 97.5% after 2 days, to 83.2% after 6 days, to 81.3% after 8 days and to 68% after 15 days (pH 2.79).

Example 58

Preparation of Bromourea from Sodium Bromate, Sodium Bromide, and HBr 48% in the Presence of Urea (2.06/30.6 $Br_2$/Urea)

Urea (35 g, 582.7 mmol) and NaBr (1008 mg, 9.8 mmol) and $NaBrO_3$ (759 mg, 5 mmol) were dissolved in $H_2O$ (74.2 g) in a 250 ml three neck flask (pH 10.36). Then 3.3 g aq. 48% HBr solution (19.4 mmol HBr) was added during 5 min to produce a yellowish solution retaining 2.06% as total $Br_2$ (pH 1.8). After 22 hours 99.5% of the original active Br2 (total) was observed (pH 2.53) which decreased to 98.5% after 2 days (pH 2.73), to 88.8% after 6 days (pH 2.7), to 84% after 8 days, and to 72.3% after 15 days.

Example 59

Preparation of Bromourea Composition from Bromourea and Chlorourea (1:1 Molar Ratio Bromourea:Chlorourea)

5 g of a solution of chlorourea, 1.63% active $Cl_2$ (total) was mixed with 7.33 g of a solution of 2.51% active $Br_2$ in a dark bottle to produce a yellowish solution with 2.97% $Br_2$ (total) with pH 2.14. UV (277 nm).

Example 60

Microbial Efficacy of Chlorourea and Bromourea Prepared from Chlorourea+NaBr at Different Concentrations and Under Different TOC Loading Materials and Methods:

Inoculum of bacteria (Activated sludge taken from Domestic Waste Water treatment Plant—Haifa).

*Pseudomonas aeruginosa* (ATCC 15442)

R2A agar for general counting.

Tryptone, in amounts 0.025, 0.119, and 0.239 g solid tryptone respectively, was weighed and dissolved in 1 liter of buffer.

Neutralization solution ($NaHSO_4$).

Titration solution, 7.84 g of sodium $Na_2S_2O_3 \cdot 5H_2O$ was dissolved in 1 liter distilled water.

Tested biocides.

Erlenmeyers (250 ml).

The biocidal efficacy of the antifouling composition at different organic loads of 0, 5 and 50 ppm TOC, was examined under different biocidal concentrations (2.5, 5, and 10 ppm) at pH 7.

1) 1 ml of inoculum was added to tryptone solutions (placed in 3 Erlenmeyers, 100 ml each, with different concentrations of TOC-0, 10 and 50 ppm).

2) 1 ml of each sample was inoculated on R2A agar (pour plate method). The result stands for the bacteria count at zero time.

3) For each of the tryptone concentrations (0, 10, 50 ppm TOC) an inoculum of bacteria (1 ml) and the appropriate biocide concentration were added.

4) After 30 min. of shaking (100 rpm), 1 ml of each sample was transferred to a tube filled with 9 ml of the neutralization solution. An aliquot of 1 ml was taken from this solution and added to another tube containing 9 ml of buffer solution. The solution was mixed under vortex. This operation was repeated for 4 more times.

5) 1 ml from the two lowest dilutions was inoculated on a R2A agar (by the pour plate method).

6) After the plates were incubated at 25° C. for 5-7 days, the bacteria count was recorded.

7) The above experiment was repeated with *Pseudomonas aeruginosa* ATCC 15442 (instead of using an inoculums from sludge), which is representative bacteria that form biofilms.

The results are presented in Table 5-10.

TABLE 5

% bacteria killed by bromourea at different TOC concentrations

| | Biocide conc. (ppm as $Cl_2$) | | |
|---|---|---|---|
| TOC conc. (ppm) | 2.5 | 5 | 10 |
| 0 | 99.14 | 98.59 | 99.88 |
| 10 | 95.48 | 99.64 | 99.89 |
| 50 | 7.34 | 91.16 | 97.69 |

TABLE 6

% bacteria killed by chlorourea at different TOC concentrations

| | Biocide conc. (ppm as $Cl_2$) | | |
|---|---|---|---|
| TOC conc. (ppm) | 2.5 | 5 | 10 |
| 0 | 56.09 | 75.17 | 80.46 |
| 10 | 67.59 | 72.64 | 85.06 |
| 50 | 64.37 | 72.41 | 78.85 |

TABLE 7

% bacteria killed by bromourea prepared from activated chlorourea with NaBr (molar ratio of 1:0.25) at different TOC concentrations

| | Biocide conc. (ppm as $Cl_2$) | | |
|---|---|---|---|
| TOC conc. (ppm) | 2.5 | 5 | 10 |
| 0 | 98.63 | 99.84 | 99.83 |
| 10 | 72.54 | 95.54 | 99.49 |
| 50 | 62.95 | 79.02 | 89.17 |

TABLE 8

% bacteria killed by bromourea, prepared from activated chlorourea with NaBr (molar ratio of 1:0.5) at different TOC concentrations

| | Biocide conc. (ppm as $Cl_2$) | | |
|---|---|---|---|
| TOC conc. (ppm) | 2.5 | 5 | 10 |
| 0 | 99.80 | 99.88 | 99.86 |
| 10 | 91.70 | 99.17 | 99.87 |
| 50 | 71.95 | 90.57 | 97.62 |

TABLE 9

% bacteria killed by bromourea, prepared from activated chlorourea with NaBr (molar ratio of 1:0.75) at different TOC concentrations

| | Biocide conc. (ppm as $Cl_2$) | | |
|---|---|---|---|
| TOC conc. (ppm) | 2.5 | 5 | 10 |
| 0 | 99.54 | 98.91 | 99.76 |
| 10 | 95.82 | 99.73 | 99.77 |
| 50 | 48.96 | 90.24 | 99.22 |

TABLE 10

% bacteria killed by bromourea, prepared from activated chlorourea with NaBr (molar ratio of 1:1) at different TOC concentrations

| TOC conc. (ppm) | Biocide conc. (ppm as $Cl_2$) | | |
|---|---|---|---|
| | 2.5 | 5 | 10 |
| 0 | 99.88 | 99.86 | 99.87 |
| 10 | 90.90 | 99.58 | 99.88 |
| 50 | 69.99 | 94.46 | 99.77 |

Additional experiments were carried out to compare the activity of other biocides: Activated NaBr with NaOCl (i.e. NaOBr), NaOCl.

The results are given in Tables 11-12, respectively.

TABLE 11

% bacteria killed by activated NaBr* compositions at different TOC concentrations

| TOC conc. (ppm) | Biocide conc. (ppm as $Cl_2$) | | |
|---|---|---|---|
| | 1 | 2.5 | 5 |
| 0 | 98.9 | 98 | 99.5 |
| 10 | 36.1 | 84.6 | 96.5 |
| 50 | 0 | 19.2 | 45.4 |

*NaBr activated with NaOCl creating NaOBr solution;

TABLE 12

% bacteria killed by NaOCl compositions at different TOC concentrations

| TOC conc. (ppm) | Biocide conc. (ppm as $Cl_2$) | | |
|---|---|---|---|
| | 1 | 2.5 | 5 |
| 0 | 54.1 | 95.5 | 99.6 |
| 10 | 3.7 | 34.6 | 97.1 |
| 50 | 0 | 12.7 | 65.9 |

Microbial efficacy of different biocides against *Pseudomonas aeruginosa* (ATCC 15442) replacing the use activated sludge bacteria. The results are given in tables 13-15.

TABLE 13

% bacteria killed by bromourea used against *Pseudomonas aeruginosa* (ATCC 15442) at different TOC concentrations

| TOC conc. (ppm) | Biocide conc. (ppm as $Cl_2$) | | |
|---|---|---|---|
| | 2.5 | 5 | 10 |
| 0 | 100 | 100 | 100 |
| 10 | 100 | 100 | 100 |
| 50 | 0 | 99.36 | 100 |
| 100 | 0 | 7.14 | 100 |

TABLE 14

% bacteria killed by use of chlorourea against *Pseudomonas\ aeruginosa* (ATCC 15442) at different TOC concentrations

| TOC conc. (ppm) | Biocide conc. (ppm as $Cl_2$) | | |
|---|---|---|---|
| | 2.5 | 5 | 10 |
| 0 | 93.33 | 99.33 | 100 |
| 10 | 93.77 | 99.77 | 100 |
| 50 | 94.93 | 99.81 | 100 |
| 100 | 94.20 | 99.77 | 100 |

TABLE 15

% bacteria killed by NaOCl used against *Pseudomonas aeruginosa* (ATCC 15442) at different TOC concentrations

| TOC conc. (ppm) | Biocide conc. (ppm as $Cl_2$) | | |
|---|---|---|---|
| | 2.5 | 5 | 10 |
| 0 | 100 | 100 | 100 |
| 10 | 43.10 | 100 | 100 |
| 50 | 17.24 | 18.97 | 100 |
| 100 | 0 | 27.59 | 90.86 |

Biocidal Activity Against Simulated Biofilm Systems (Alginate Beads)

A biofilm simulation system, alginate beads, developed by the Biofilm Bozeman Institute Montana (Grobe, K. J, Zahller, J and Stewart P. S., 2002 in "Role of dose concentration in biocide efficacy against *Pseudomonas aeruginosa* Biofilms", J. Industrial Microbiology & Biotechnology, vol. 29, pp 10-15), was used in order to evaluate the efficacy of bromine/urea against biofilm.

Preparation of the Alginate Beads

The biofilm simulation was created by entrapping bacteria in alginate gel beads. A plate of R2A agar was streaked with *Pseudomonas aeruginosa* (ATCC 15442) and incubated at 35° C. overnight. Buffer phosphate at pH 7.2 was used to scrap off the bacteria from the agar plate and to create a suspension. The bacterial suspension was mixed with an equal volume of an aqueous 4% sodium alginate solution, to make a final 2% alginate solution. The alginate and bacterial slurry were placed in a 50 ml syringe attached to a gauge needle (22), connected to a compressed air tank, allowing the syringe to be pressurized. At 20 psig pressure a stream of small drops was forced out and dropped into a stirred solution of 50 mM $CaCl_2$. The $Ca^{+2}$ hardened the alginate, and semi solid beads with entrapped bacterial cells were formed. The beads were allowed to stir in the $CaCl_2$ solution for about 20 minutes, and then rinsed in a dilute 5 mM $CaCl_2$ solution. Several flasks containing 100 beads each were incubated overnight at 35° C. on a rotating shaker in a buffer solution (at pH 7) with 5 mM addition of $CaCl_2$ to maintain the beads structure. The resulting beads diameter is about 2 mm.

General Description of the Experiment

At the beginning of the experiment, the supernatant of the beads buffer suspension containing 5 mM $CaCl_2$ was decanted and replaced by the 100 ml biocide solution with the required concentration (Urea-bromine compositions prepared by dissolving urea 15.02 g (250.3 mmol, 15% concentration) and 1.17 g $Br_2$ (7.32 mmol, 1.17% concentration) in 84 g $H_2O$ (34.2:1 urea:$Br_2$ molar ratio). After different interval contact times, 10 beads were removed and placed in a 5 g/l sodium thiosulfate solution containing 50 mM sodium citrate. The sodium citrate was used to dissolve the alginate gel and release the bacteria into the solution. The neutralizer-citrate solution was placed in the refrigerator for 2 hours, than diluted and placed on R2A agar plates using pour plate technique. The plates were incubated at 35° C. for 24-48 hours and counted. The efficacy and toxicity of the neutralizer were checked as well as a control experiment without biocide addition. Four concentrations (0.5, 1, 2.5 and 5 ppm) were tested at four different contact times (5, 15, 30, and 60 min). Tables 16-22 describe the surviving colony forming units (CFU) of the bacteria after different biocides treatment at different contact times. In addition, the efficacy of bromourea from chlorourea and NaBr (1:0.5 molar ratio) was tested at the same concentrations (mentioned above) and after a long contact time of 24 hours (Table 23).

TABLE 16

Biocidal efficacy of a bromine urea composition against bacterial beads (survival of bacteria (CFU) as a function of biocide loading and contact time)

| Contact Time | Biocide concentration (ppm as Cl2) | | | |
|---|---|---|---|---|
| | 0.5 | 1 | 2.5 | 5 |
| 0 | $6.00 \times 10^6$ | $6.00 \times 10^6$ | $6.00 \times 10^6$ | $6.00 \times 10^6$ |
| 5 | $5.45 \times 10^6$ | $6.00 \times 10^6$ | $2.15 \times 10^6$ | $1.63 \times 10^5$ |
| 15 | $4.85 \times 10^6$ | $2.13 \times 10^6$ | $1.30 \times 10^4$ | $1.00 \times 10^0$ |
| 30 | $4.10 \times 10^6$ | $4.35 \times 10^5$ | $1.00 \times 10^0$ | $1.00 \times 10^0$ |
| 60 | $1.45 \times 10^6$ | $2.30 \times 10^4$ | $1.00 \times 10^0$ | $1.00 \times 10^0$ |

TABLE 17

Biocidal efficacy of a chlorourea against bacterial beads (survival of bacteria (CFU) as a function of biocide loading and contact time)

| Contact Time | Biocide concentration (ppm as Cl$_2$) | | | |
|---|---|---|---|---|
| | 0.5 | 1 | 2.5 | 5 |
| 0 | $8.40 \times 10^7$ | $8.40 \times 10^7$ | $8.40 \times 10^7$ | $8.40 \times 10^7$ |
| 5 | $5.90 \times 10^6$ | $7.50 \times 10^6$ | $7.80 \times 10^6$ | $6.70 \times 10^6$ |
| 15 | $5.30 \times 10^6$ | $7.20 \times 10^6$ | $2.60 \times 10^6$ | $6.50 \times 10^4$ |
| 30 | $5.60 \times 10^6$ | $9.40 \times 10^5$ | $2.21 \times 10^3$ | $1.00 \times 10^0$ |
| 60 | $2.25 \times 10^6$ | $9.13 \times 10^2$ | $1.00 \times 10^0$ | $1.00 \times 10^0$ |

TABLE 18

Biocidal efficacy of a bromourea from chlorourea and NaBr (1:1 molar ratio) against bacterial beads (survival of bacteria (CFU) as a function of biocide loading and contact time)

| Contact Time | Biocide concentration (ppm as Cl$_2$) | | | |
|---|---|---|---|---|
| | 0.5 | 1 | 2.5 | 5 |
| 0 | $1.00 \times 10^7$ | $1.00 \times 10^7$ | $1.00 \times 10^7$ | $1.00 \times 10^7$ |
| 5 | $8.90 \times 10^6$ | $7.20 \times 10^6$ | $1.80 \times 10^6$ | $6.30 \times 10^3$ |
| 15 | $5.90 \times 10^5$ | $6.00 \times 10^6$ | $1.00 \times 10^0$ | $1.00 \times 10^0$ |
| 30 | $3.47 \times 10^6$ | $2.70 \times 10^4$ | $1.00 \times 10^0$ | $1.00 \times 10^0$ |
| 60 | $5.30 \times 10^5$ | $1.00 \times 10^0$ | $1.00 \times 10^0$ | $1.00 \times 10^0$ |

TABLE 19

Biocidal efficacy of bromomourea from chlorourea and KBr (molar ratio of 1:1) against bacterial beads (survival of bacteria (CFU) as a function of biocide loading and contact time)

| Contact Time | Biocide concentration (ppm as Cl$_2$) | | | |
|---|---|---|---|---|
| | 0.5 | 1 | 2.5 | 5 |
| 0 | $1.80 \times 10^7$ | $1.80 \times 10^7$ | $1.80 \times 10^7$ | $1.80 \times 10^7$ |
| 5 | $6.45 \times 10^6$ | $7.20 \times 10^6$ | $2.00 \times 10^6$ | $6.30 \times 10^4$ |

TABLE 19-continued

Biocidal efficacy of bromomourea from chlorourea and KBr (molar ratio of 1:1) against bacterial beads (survival of bacteria (CFU) as a function of biocide loading and contact time)

| Contact Time | Biocide concentration (ppm as Cl$_2$) | | | |
|---|---|---|---|---|
| | 0.5 | 1 | 2.5 | 5 |
| 15 | $3.57 \times 10^6$ | $1.14 \times 10^6$ | $2.00 \times 10^0$ | $1.00 \times 10^0$ |
| 30 | $2.15 \times 10^6$ | $2.80 \times 10^4$ | $1.00 \times 10^0$ | $1.00 \times 10^0$ |
| 60 | $2.42 \times 10^5$ | $1.00 \times 10^0$ | $1.00 \times 10^0$ | $1.00 \times 10^0$ |

TABLE 20

Biocidal efficacy of bromomourea (2% as Br2 total) prepared from sodium bromate and HBr/NaBr (2:1 molar ratio) in the presence of urea 30.6% wt, against bacterial beads (survival of bacteria (CFU) as a function of biocide loading and contact time)

| Contact Time | Biocide concentration (ppm as Cl$_2$) | | | |
|---|---|---|---|---|
| | 0.5 | 1 | 2.5 | 5 |
| 0 | $1.00 \times 10^7$ | $1.00 \times 10^7$ | $1.00 \times 10^7$ | $1.00 \times 10^7$ |
| 5 | $9.50 \times 10^6$ | $1.00 \times 10^7$ | $1.00 \times 10^6$ | $2.50 \times 10^1$ |
| 15 | $8.80 \times 10^6$ | $3.30 \times 10^6$ | $4.00 \times 10^2$ | $1.00 \times 10^0$ |
| 30 | $4.00 \times 10^6$ | $9.00 \times 10^5$ | $1.00 \times 10^0$ | $1.00 \times 10^0$ |
| 60 | $6.20 \times 10^5$ | $1.20 \times 10^6$ | $1.00 \times 10^0$ | $1.00 \times 10^0$ |

TABLE 21

Biocidal efficacy of NaOCl against bacterial beads (survival of bacteria (CFU) as a function of biocide loading and contact time)

| Contact Time | Biocide concentration (ppm as Cl2) | | | |
|---|---|---|---|---|
| | 0.5 | 1 | 2.5 | 5 |
| 0 | $8.00 \times 10^6$ | $8.00 \times 10^6$ | $8.00 \times 10^6$ | $8.00 \times 10^6$ |
| 5 | $7.90 \times 10^6$ | $4.40 \times 10^6$ | $3.60 \times 10^6$ | $1.74 \times 10^6$ |
| 15 | $5.65 \times 10^6$ | $3.30 \times 10^6$ | $1.83 \times 10^6$ | $6.80 \times 10^6$ |
| 30 | $4.72 \times 10^6$ | $2.15 \times 10^6$ | $7.60 \times 10^6$ | $3. \times 10^6$ |
| 60 | $5.00 \times 10^6$ | $1.20 \times 10^6$ | $1.95 \times 10^5$ | $1.00 \times 10^0$ |

TABLE 22

Biocidal efficacy activated NaBr (with NaOCl) against bacterial beads (survival of bacteria (CFU) as a function of biocide loading and contact time)

| Contact Time | Biocide concentration (ppm as Cl$_2$) | | | |
|---|---|---|---|---|
| | 0.5 | 1 | 2.5 | 5 |
| 0 | $6.00 \times 10^6$ | $6.00 \times 10^6$ | $6.00 \times 10^6$ | $6.00 \times 10^6$ |
| 5 | $9.00 \times 10^6$ | $2.75 \times 10^6$ | $2.47 \times 10^6$ | $2.53 \times 10^6$ |
| 15 | $1.85 \times 10^6$ | $2.00 \times 10^6$ | $7.10 \times 10^5$ | $2.35 \times 10^5$ |
| 30 | $2.10 \times 10^6$ | $1.00 \times 10^6$ | $2.10 \times 10^5$ | $2.70 \times 10^2$ |
| 60 | $1.45 \times 10^6$ | $3.30 \times 10^5$ | $1.25 \times 10^2$ | $1.20 \times 10^1$ |

TABLE 23

Biocidal efficacy of a bromourea from chlorourea and NaBr (1:0.5 molar ratio) against bacterial beads (survival of bacteria (CFU) as a function of biocide loading after a contact time of 24 hours)

| Contact Time | Biocide concentration (ppm as $Cl_2$) | | | |
|---|---|---|---|---|
| | 0.5 | 1 | 2.5 | 5 |
| 0 | $1.60 \times 10^7$ | $1.60 \times 10^7$ | $1.60 \times 10^7$ | $1.60 \times 10^7$ |
| 24 hours | $1.25 \times 10^3$ | $1.00 \times 10^0$ | $1.00 \times 10^0$ | $1.00 \times 10^0$ |

While this invention has been described in terms of some specific examples, many modifications and variations are possible. It is therefore understood that within the scope of the appended claims, the invention may be realized otherwise than as specifically described.

The invention claimed is:

1. A process of removing biofouling or preventing biofouling or disinfecting in a volume of an aqueous liquid or on a surface in contact with an aqueous liquid, consisting of the steps of
   i) providing an aqueous composition wherein the aqueous composition is an antifouling or biocidal stock solution containing urea and an active halogen source, wherein the active halogen source comprises an active bromine source, the active bromine source comprises an oxidizer wherein the oxidizer comprises a hypochlorite, wherein the molar ratio urea/halogen is at least 1/1, the halogen concentration measured as active chlorine is from 1,000 ppm to 100,000 ppm, and the pH of said aqueous composition is less than 4; and
   ii) contacting said volume or said surface with said stock solution or with an aqueous dilution thereof,
   wherein said stock solution is sulfamate free and alkali caustic free, and is stable on prolonged storage for up to two years.
2. The process according to claim 1, wherein said active bromine source consists of HBr with the oxidizer in a molar ratio of from 1.0 to 2.0, wherein the molar ratio of urea/total bromine is at least 2/1, and the pH value of said aqueous composition is less than 3.
3. The process according to claim 1 consisting of
   i) providing said aqueous composition by mixing water, urea, and an active bromine source comprising a mixture of HBr with the oxidizer, wherein the molar ratio urea/total bromine is greater than about 4/1, the composition being a stock solution of stabilized active bromine;
   ii) optionally diluting said stock solution obtained in step i) with water, thereby obtaining a working solution; and
   iii) contacting said volume or said surface with said stock solution or with said dilution thereof.
4. The process according to claim 2, wherein the molar ratio urea/bromine is up to 40/1.
5. The process according to claim 1, wherein said stock solution comprises halogen in a concentration of 0.1-20 wt %, and wherein said stock solution is stable on prolonged storage for up to two years.
6. The process according to claim 1, wherein said aqueous dilution of the stock solution exhibits biocidal activity when diluted down to an active bromine concentration of 0.1 ppm.
7. The process according to claim 1, for treating water with high TOC content.
8. The process according to claim 1, wherein said surface comprises irrigation pipes, waste water, industrial cooling water, process water, and equipment in the Pulp & Paper industry.
9. The process according to claim 1, wherein said antifouling composition unclogs pierced irrigation pipes and fertilizes the irrigated plot.
10. The process according to claim 1, wherein said aqueous composition further contains salts with additional fertilizing and/or stabilizing properties.
11. The process according to claim 1, wherein said step of providing the antifouling composition is a batch procedure.
12. The process according to claim 1, wherein said step of providing the antifouling composition is a continuous procedure.

* * * * *